United States Patent [19]

Heaton

[11] Patent Number: 5,112,451
[45] Date of Patent: May 12, 1992

[54] ELECTROCHEMICAL PREPARATION OF IRON NITROSYL CARBONYL AND ITS USE AS A CATALYST

[75] Inventor: Duane E. Heaton, Lake Jackson, Tex.

[73] Assignee: The Dow Chemical Company, Midland, Mich.

[21] Appl. No.: 578,110

[22] Filed: Sep. 5, 1990

Related U.S. Application Data

[63] Continuation-in-part of Ser. No. 348,625, May 8, 1989, Pat. No. 4,973,568.

[51] Int. Cl.⁵ .................... C25B 1/00; C25B 3/04
[52] U.S. Cl. .......................... 204/86; 204/91; 502/161; 502/174; 502/200
[58] Field of Search ..................... 204/86, 91

[56] References Cited

U.S. PATENT DOCUMENTS

| | | | |
|---|---|---|---|
| 2,473,993 | 6/1949 | Gresham et al. | 502/161 |
| 3,377,397 | 4/1968 | Maxfield | 585/369 |
| 3,448,129 | 6/1969 | Maxfield | 556/28 |
| 3,481,710 | 12/1969 | Maxfield | 423/386 |
| 3,551,467 | 12/1970 | Akakawa et al. | 556/140 |
| 3,954,665 | 5/1976 | Tkatchenko | 252/428 |
| 4,006,168 | 2/1977 | Kerr | 252/411 |
| 4,144,278 | 3/1979 | Strope | 423/386 |
| 4,181,707 | 1/1980 | Strope | 423/386 |
| 4,234,454 | 11/1980 | Strope | 252/430 |
| 4,238,301 | 12/1980 | Petit et al. | 204/72 |
| 5,057,469 | 10/1991 | Heaton | 502/24 |

OTHER PUBLICATIONS

D. Ballivet-Tkatchenko, Inorganica Chimica Acta, vol. 30, pp. 2-289-L290 (1978).
P. L. Maxfield, Inorg. Nucl. Chem. Letters vol. 6, pp. 707-711 (1970).
J. P. Candlin, et al., J. Chem. Soc. (C), pp. 1856-1860 (1968).
I. Tkatchenko, Journal of Organometallic Chemistry, vol. 124, pp. C39-C42, (1977).
Gerald E, Gadd, et al., Organometallics, pp. 391-397 (1987).
A. Mortreux et al., Applied Catalysis, vol. 24, pp. 1-15 (1986).

Primary Examiner—T. Tung
Assistant Examiner—David G. Ryser

[57] ABSTRACT

Iron nitrosyl carbonyl is prepared by electrochemically reducing either an iron nitrosyl halide or a mixture of iron chloride and a source of NO in the presence of CO. Constant current or constant potential is used to effect the reduction.

9 Claims, No Drawings

5,112,451

ELECTROCHEMICAL PREPARATION OF IRON NITROSYL CARBONYL AND ITS USE AS A CATALYST

CROSS REFERENCE TO RELATED APPLICATION

This application is a continuation-in-part of application Ser. No. 07/348,625 filed May 8, 1989, now U.S. Pat. No. 4,973,568.

BACKGROUND OF THE INVENTION

The present invention relates to a process for the preparation of iron nitrosyl carbonyl, more particularly electrochemical preparation thereof.

The complex iron nitrosyl carbonyl [Fe(NO)$_2$(CO)$_2$] is known to dimerize butadiene to produce vinyl cyclohexene (VCH). Methods known to prepare various iron nitrosyl complexes require reduction of [Fe(NO)$_2$Cl]$_2$ or reaction of nitric oxide (NO) on a mixture of iron and FeCl$_3$. Reference to these methods is found in U.S. Pat. No. 4,238,301. Another patent, U.S. Pat. No. 4,234,454, discloses the preparation of various metal nitrosyl catalytic solutions by employing the combination of manganese, zinc or tin together with iron, cobalt or nickel nitrosyl halides to produce the respective metal nitrosyls in a system for dimerizing various conjugated dienes. An earlier patent, U.S. Pat. No. 3,510,533, discloses the dimerization of conjugated dienes with n-allyldinitrosyliron complexes and a method for their preparation. Several methods are given involving the reduction of a $\mu,\mu'$-dihalo-tetranitrosyldiiron.

The methods of reduction known to the art have numerous disadvantages. Some of these are: (1) the reduction of the metal nitrosyl compound is required to be in the presence of the butadiene. (2) many of the reducing agents themselves will polymerize the butadiene, (3) contaminants are introduced by the reducing agents and (4) catalyst solutions cannot be stored and expected to retain their activity.

The dimerized products of the process of the invention may be useful in themselves or as intermediates to other products. Thus, for example, 4-VCH can be (1) chlorinated to make an insecticide, (2) oxidized to make benzoic acid, (3) reacted with hydrogen sulfide in the presence of acid-type catalysts to make sulfur containing resins and (4) reacted with hydrogen sulfide in the presence of ultraviolet light to make a $\beta$-mercaptoethyl cyclohexane.

SUMMARY OF THE INVENTION

The present invention is a process for preparing iron nitrosyl carbonyl by electrochemically reducing either an iron nitrosyl halide or a mixture of iron chloride and a source of NO in the presence of CO.

DETAILED DESCRIPTION OF THE INVENTION

In general, the catalysts of this invention are suitable for dimerizing to cyclic products the class of conjugated diolefins. While butadiene is exemplified to make 4-VCH other conjugated dienes can be cyclized similarly. Thus, isoprene and other conjugated diolefins can be dimerized to cyclic compounds.

While ferrous chloride is the preferred compound to be employed in forming the complex used in the catalyst of the invention, other compounds are useful in preparing the catalysts. Thus, for example, [Fe(NO)$_2$Cl]$_2$, FeCl$_3$ and the like are useful for the preparation. Analogous compounds of cobalt and nickel are useful in preparing the analogous catalysts, but such catalysts are not as active as the iron catalysts.

Other reducing agents besides tin which are useful include zinc, manganese, magnesium and the like, or an electrolytic cell may be used in the reduction.

The process of the invention is effected by electrolysis of iron nitrosylchloride or an iron chloride and a source of NO (such as NO gas or NaNO$_2$) in an electrochemical cell in the presence of carbon monoxide. Advantageously, the potential is maintained at a constant level relative to a reference electrode with the aid of a potentiostat which automatically regulates the voltage and the current between the anode and the cathode. Alternatively the reference electrode may be omitted and the current between the anode and cathode held constant in a manner known in the art.

The reaction is effected in the presence of a suitable solvent and optionally in the presence of an electrolyte, which makes it possible to operate with a lower initial voltage between the anode and the cathode.

While any electrochemical apparatus in which the reduction takes place is suitable, the type of electrochemical cell preferred for use in the process of the invention using constant potential comprises three electrodes: a cathode, an anode and a reference electrode. In the constant current process of this invention, the type of electrochemical cell preferred comprises two electrodes; a cathode and an anode. The cathode is made of a material which is inert to the reaction medium. The cathode is advantageously made of platinum and a preferred form of the cathode is a platinum wire mesh. Other suitable cathode materials include materials which are relatively inert under the reducing conditions of the process such as vitreous carbon, iron or nickel. The anode is suitably made of an oxidizable metal. Suitable anode materials are any which can be oxidized, preferably iron, tin, zinc, magnesium, aluminum, or manganese, more preferably aluminum or iron. According to a particularly preferred embodiment of the invention, the anode is a hollow cylinder made of iron or aluminum and the cathode is a cylindrical platinum wire mesh or other high surface area material which is exterior to and concentric to the anode. The reference electrode, when used, may be selected from electrodes within the skill in the art, such as Ag/AgCl, Ag/Ag$^+$, and calomel. Alternatively the reference electrode may be a Ag wire or similar nonreactive metal whose potential has been determined relative to one of the other above mentioned reference electrodes in a manner known in the art. It is preferable to locate the reference electrode in the vicinity of the cathode.

The electrochemical solvent used in the process of the invention must be inert to both the reactants and to the reaction conditions. Any such solvent in which all of the reactants are at least partially soluble is suitable. The solvent preferably has a fairly high dielectric constant, e.g. above 5.0. Suitable solvents include ethylene carbonate, tetrahydrofuran, diglyme, acetonitrile, dimethyl formamide (DMF) and formamide. A particularly preferred solvent is propylene carbonate.

If an electrolyte is used, it must be soluble in the solvent used for the reaction. Suitable such electrolytes include lithium salts or quaternary ammonium salts, such as LiCl, LiClO$_4$, or quaternary alkyl/aryl ammonium chlorides or perchlorates, such as tetrabutylammonium perchlorate.

The iron nitrosyl halide, preferably dinitrosyliron chloride, used in the present process may be prepared by means within the skill in the art, in particular according to the following reaction:

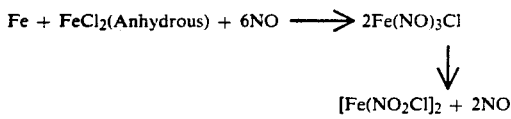

$$Fe + FeCl_2(Anhydrous) + 6NO \longrightarrow 2Fe(NO)_3Cl$$
$$\downarrow$$
$$[Fe(NO_2Cl]_2 + 2NO$$

Alternatively, the comound may be prepared by the reaction of a source of nitric oxide (NO) (e.g. NaNO$_2$) with an iron chloride and iron metal. If desired, the product obtained may be further purified by means within the skill in the art e.g., sublimation.

The iron chloride used is either ferrous chloride, FeCl$_2$, or ferric chloride, FeCl$_3$. The salts are optionally dried before use.

The source of NO (the nitrosyl radical) is advantageously a nitrite salt, preferably an alkali metal or alkaline earth metal nitrite salt, e.g. sodium nitrite or a nitrogen oxide, preferably nitric oxide. The nitrite salts and nitrogen oxides are commercially available. Nitric oxide, NO, is preferably used in the gaseous state, and is advantageously the commercially available liquified bottled gas.

The mole ratio of iron halide to source of NO is suitably from about 3:1 to about 1:5, preferably from about 1:1 to about 1:3.

The carbon monoxide (CO) is suitably obtained from any source, e.g. commercially as a liquid (under pressure) or a gas, or obtained chemically, e.g. from reaction of calcium carbonate with zinc dust. The CO is suitably provided to the reaction by any means, advantageously by bubbling (sparging) through the reaction medium or by the reaction medium being pressurized with CO. The mixture in the cell is advantageously either stirred or circulated in some manner to provide agitation and mixing. Carbon monoxide is preferably supplied in quantities of at least about 1 mole per mole of [Fe(NO)$_2$Cl]$_2$ or FeCl$_3$, more preferably from about 2 to about 10, moles of CO to mole of [Fe(NO$_2$)Cl]$_2$ or FeCl$_3$.

Any temperature and pressure at which the reaction takes place are suitable reaction conditions but it is preferable to avoid high pressures because such pressures require special cell design and to avoid temperatures sufficiently high that there is decomposition. However, sufficient pressure to maintain CO in solution is needed. Preferred temperatures are from about 0° C. to about 250° C., more preferably from about 20° C. to about 120° C., because low temperatures slow the reaction, and higher temperatures may result in some loss by decomposition. Preferred pressures are from about 0 psig (0 kilopascals gauge) (KPag) to about 1000 psig (6891 KPag), more preferably from about 0 psig (0 KPag) because construction of electrolytic cell for pressure work is difficult. Zero psig corresponds to sparging CO through the reacting solution at atmospheric pressure. Advantageously sparging is continued at least as long as the reaction mixture is heated.

Any conditions of voltage and current in the electrolysis at which iron nitrosyl carbonyl is formed are suitable. For a constant potential process, these are conditions under which iron nitrosyl halides or iron halide/nitrosyl source mixtures are reduced, preferably wherein the cathode potential with respect to the reference electrode is at or above that corresponding to the plateau of the last reduction wave of the iron nitrosyl chloride or iron chloride/nitrosyl source mixture with CO. It is also preferable to maintain this potential below that corresponding to the plateau of the first reduction wave of the solvent.

For the constant current process, conditions are suitably any under which iron nitrosyl halides or iron halide/nitrosyl source mixtures are reduced, preferably with greater than 0 mA of current, more preferably with a high enough current to perform the desired reaction in a suitable time period. The amount of current depends on the quantity of material to be reduced. Determination of the amperage is within the skill in the art.

It is advantageous to use a potentiostat to maintain a constant cathode potential relative to the reference electrode, in a manner within the skill in the art. The potentiostat provides a working voltage and current between the anode and cathode which are functions of the chosen reference potential and the characteristics of the reaction medium, such as dielectric constant of the solvent and the resistivity of the reaction mixture.

In general, the preferred process comprises steps of (a) dissolving solid reactants in a suitable solvent, preferably with mixing;

(b) placing the solvent into an electrochemical cell having an anode and a cathode;

(c) adding gaseous reactants, advantageously by bubbling or by pressure;

(d) applying sufficient current or potential between anode and cathode such that there is reaction to form iron nitrosyl carbonyl; and, preferably, (e) allowing the reaction to reach a predetermined degree of completeness.

The solid reactants are iron nitrosyl halide or a mixture of iron chloride and, optionally, a source of NO as sodium nitrite. Alternatively a gaseous NO is used. CO is also a gaseous reactant. These steps are suitably performed in any effective order or simultaneously, for instance step (a) optionally preceeds or follows step (b).

Advantageously, the reaction is allowed to continue to completion. The reaction is considered complete when consective samples analyzed, e.g. using infrared (IR) spectroscopy, show no significant increase in Fe(-NO)$_2$(CO)$_2$. Alternatively, when the reaction is run at constant potential, the reaction is considered complete when the current drops to a value considered negligible compared to the starting current, e.g. (a value 1% of the starting current).

The product is suitably used without purification or purified by means within the skill in the art, e.g. sublimation, followed by condensing in a cold trap. Product is also suitably purified by dissolution or preparation in a solvent for the catalyst such as diglyme and subsequent separation by addition of a miscible non-solvent for the catalyst such as water or octane, such as is taught in copending U.S. application Ser. No. 07/578,108 filed Sep. 5, 1990, now U.S. Pat. No. 5,057,469, which is incorporated by reference herein its entirety.

The iron nitrosyl carbonyl is particularly useful for dimerizing butadiene into vinyl cyclohexene. Conditions for the dimerization are within the skill in the art and are operable with the catalysts prepared by the process of the present invention. Temperature ranges are preferably from about 20° to about 175° C.; pressure ranges are from about atmospheric to about 1,000 psig (6891 KPag); and the reaction is preferably conducted for a period of time of from about 10 minutes to about 48 hours.

The following example is representative of the catalyst preparation and its use. All percentages, ratios and parts are by weight unless designated otherwise.

EXAMPLE 1

Catalyst Preparation

A glass vessel is used as an electrolytic cell. It is equipped with a magnetic stirrer, three ports containing electrodes, a vent, and a gas addition port fitted with a tube extending below the solution level to allow gas to bubble through the liquid. The anode is a hollow aluminum cylinder. The cathode is a platinum wire mesh surrounding but not contacting the anode, and the reference electrode is a standard calomel electrode also near the cathode.

In a drybox, the cell is loaded with 100 mL, (milliliters) of propylene carbonate solution containing 2.5 g (grams) $FeCl_3$ and 3.2 g $NaNO_2$ (sodium nitrite) and is sealed. The solution is stirred; CO is bubbled through the solution using the gas inlet tube and vented through the reactor vent to prevent pressurization. A potentiostat is used to apply a cathode potential of $-1000$ millivolts relative to the reference electrode. The initial current is monitored. The current is observed to decrease. The reaction is stopped when the current reaches 5% of its initial value. The reaction is considered 95% complete at this point.

This solution is suitable for use as a dimerization catalyst.

What is claimed is:

1. A process for preparing iron nitrosyl carbonyl by electrochemically reducing either an iron nitrosyl halide or a mixture of iron chloride and a source of NO in the presence of CO.

2. The process of claim 1 wherein an iron nitrosyl halide is used and the halide is iron nitrosyl chloride.

3. The process of claim 1 wherein an iron chloride and a source of NO is used.

4. The process of claim 3 wherein the iron chloride is ferric chloride or ferrous chloride and the source of NO is nitric oxide.

5. The process of claim 3 wherein the iron chloride is ferric chloride or ferrous chloride and the source of NO is an alkali or alkaline earth metal nitrite salt.

6. The process of claim 1 wherein the electrochemical reduction takes place at a constant potential.

7. The process of claim 1 wherein the electrochemical reduction takes place at a constant current.

8. The process of claim 1 wherein the electrochemical reduction comprises the following steps: (a) dissolving solid reactants in a suitable solvent; (b) placing the solvent into an electrochemical cell having an anode and cathode; (c) adding gaseous reactants; (d) applying current or potential between the anode and the cathode such that there is reaction to form iron nitrosyl carbonyl.

9. The process of claim 8 additionally comprising the step of (e) allowing the reaction to reach a predetermined degree of completeness.

* * * * *